United States Patent [19]

Masuta et al.

[11] Patent Number: 5,304,731
[45] Date of Patent: Apr. 19, 1994

[54] VECTOR

[75] Inventors: Chikara Masuta; Yoichi Takanami; Akira Koiwai, all of Yokohama, Japan

[73] Assignee: Japan Tobacco Inc., Tokyo, Japan

[21] Appl. No.: 944,710

[22] Filed: Sep. 11, 1992

Related U.S. Application Data

[63] Continuation of Ser. No. 390,990, Aug. 9, 1989, abandoned.

[30] Foreign Application Priority Data

Aug. 17, 1988 [JP] Japan ................. 63-203119

[51] Int. Cl.$^5$ ............... A01H 1/04; C12N 15/00; C12N 7/00; C12P 19/34
[52] U.S. Cl. ................... 800/205; 435/91.33; 435/172.3; 435/235.1; 435/320.1
[58] Field of Search ............ 435/69.1, 70.1, 172.3, 435/235.1, 320.1, 91; 935/25, 35, 64, 67; 800/205

[56] References Cited

U.S. PATENT DOCUMENTS 4,885,248 12/1989 Ahlquist .................... 435/172.3

FOREIGN PATENT DOCUMENTS

| | | | |
|---|---|---|---|
| 8707644 | 12/1987 | World Int. Prop. O. ... | C12N 15/00 |
| 8908145 | 9/1989 | World Int. Prop. O. ... | C12N 15/00 |
| 9000611 | 1/1990 | World Int. Prop. O. ... | C12N 15/73 |
| 9012107 | 10/1990 | World Int. Prop. O. .... | C12P 21/02 |
| 9013654 | 11/1990 | World Int. Prop. O. ... | C12N 15/83 |

OTHER PUBLICATIONS

Collmer et al. 1986, Biochem. Biophys. Res. Commun. 135(1): 290–296.
Takamatsu et al. 1987, EMBO J. 6(2): 307–311.
French et al. 1986, Science 231: 1294–1297.
Gonsalves et al. 1982, Phytopathology 72: 1533–1538.
Masuta et al. 1988, J. Biochem. 104: 841–846.
Masuta et al. 1987, Nucl. Acids Res. 15(23): 10048.
Harrison et al. 1987, Nature 328: 799–805.
Kuwata et al. 1988, Ann. Phytopath Soc. Japan 54(4): 510–515.
"Infectious Transcripts From a cDNA Clone of Satellite RNA (Strain Y) of Cucumber Mosaic Virus (CMV)", Abstract, 5th International Congress of Plant Pathology, Aug. 20–27, 1988 (Japan)-Chikara Masuta-co-author.

*Primary Examiner*—David T. Fox
*Attorney, Agent, or Firm*—Beveridge, DeGrandi, Weilacher & Young

[57] ABSTRACT

This invention relates to a novel vector constructed by inserting an exogenous RNA fragment into a vector comprising a satellite RNA of a plant virus in a way wherein the replication ability of the satellite is retained as much as possible to convert it to a chimeric RNA molecule. Those novel vectors satisfactorily have conditions necessary as a vector and may effectively be used for transformation of plants, synthesis of proteins and the like.

11 Claims, 4 Drawing Sheets

```
         10          20          30          40          50          60
    GUUUUGUUUG  AUGGAGAAUU  GCGUAGAGGG  GUUAUAUCUG  CGUGAGGAUC  CAUCACUCGG 70          80          90         100         110         120
    CGGUGUGGGA  UACCUCCCUG  CUAAGGCGGG  UUGAGAGUGU  AUCUCGGACU  GGAGGCGGGA 130         140         150         160         170         180
    UGUCUGCGGG  UGUUCCGUCU  GCUGCCCACG  AUGGUGGGAG  UCACCCAAGG  GCUGACUUUU 190         200         210         220         230         240
    UCAGCUCUGC  AUUUCUCAUU  UGAGCCCCCG  CUCAGUUUGC  UAGCAAAACC  CGGCACAUGG 250         260         270         280         290         300
    UUCGCCGUUA  CUAUGGAUUU  CGAAAGAAAC  ACUCUGUUAG  GUGGUAUCGU  GGAUGACGCA 310         320         330         340         350         360
    CGCAGGGAGA  AGCUAAGGCU  UAUGCUAUGC  UGAUCUCCGU  GAAUGUCUAU  ACAUUCCUCU

369
    ACAGGACCC
```

```
         10         20         30         40         50         60
     GUUUGUUUG  AUGGAGAAUU  GCGUAGAGGG  GUUAUAUCUG  CGUGAGGAUC  CAUCACUCGG
         70         80         90        100        110        120
     CGGUGUGGGA  UACCUCCCUG  CUAAGGCGGA  UUGAGAGUGU  AUCUCGGACU  GGAGGCGGGA
        130        140        150        160        170        180
     UGUCUGCGGG  UGUUCCGUCU  GCUGCCCACG  AUGGUGGGAG  UCACCCAAGG  GCUGACUUUU
        190        200        210        220        230        240
     UCAGCUCUGC  AUUUCUCAUU  UGAGCCCCCG  CUCAGUUUGC  UAGCAAAACC  CGGCACAUGG
        250        260        270        280        290        300
     UUCGCCGUUA  CUAUGGAUUU  CGAAAGAAAC  ACUCUGUUAG  GUGGUAUCGU  GGAUGACGCA
        310        320        330        340        350        360
     CGCAGGGAGA  AGCUAAGGCU  UAUGCUAUGC  UGAUCUCCGU  GAAUGUCUAU  ACAUUCCUCU
        369
     ACAGGACCC
```

VECTOR

This application is a continuation, of application number of 07/390,990, filed 08/09/89, now abandoned which application is entirely incorporated herein by reference.

BACKGROUND OF THE INVENTION

This invention relates to a vector comprising a satellite RNA of a plant virus.

It is known that so-called satellites have relatively low molecular weight (e.g., $0.1–0.5 \times 10^6$ dalton) and barely have homology with the genome RNA of the helper virus (parent virus).

So-called satellites of plant viruses are classified into two categories.

One category is satellite viruses wherein satellite RNA is coated with the coat protein which is encoded by satellite RNA, for example, satellite tobacco necrosis virus (STNV), satellite panicum mosaic virus (SPMV) and satellite tobacco mosaic virus (STMV).

The other category is satellite RNAs contained in helper virus particles, a large number of low molecular weight RNAs belong thereto, typical examples are cucumber mosaic virus (CMV) satellite RNA, tobacco ring spot virus (TobRV) satellite RNA, etc. Research on the molecular level is being vigorously carried out.

More particularly, base sequences of several strains have been determined in CMV satellite RNA and reported. For example, Hidaka et al.: FEBS Letters 174, p38–42 (1984); Garcia-Arenal et al.: Virology 158, p339–347 (1987).

Further, there has been a successful insertion of the full length cDNA of CMV satellite RNA into a DNA transcription vector and the creation of an infectious transcription product with RNA polymerase in a test tube (Collmer & Kaper: BBRC 135, p290–296 (1986); Masuta et al.: Nucl. Acids. Res. 15, p10048 (1987); Kurath & Palukaitis: Virology 159, p199–208 (1987)).

Incidentally, there have been two cases of practical trials to introduce an exogenous RNA fragment in plant cells by changing a plant RNA virus into a vector: brome mosaic virus (BMV) RNA 3 (French et al.: Science 231, p1294–1297 (1986)) and tobacco mosaic virus (TMV) RNA (Takamatsu et al.: EMBO J.6, p307–311 (1987)). In each case a recombinant transcription vector was created wherein the coat protein gene region is replaced by chloramphenicol acetyltransferase (CAT) gene.

However, in the former case, utilization of the recombinant transcription vector was limited to inoculation of a protoplast and it was impossible to infect barley as a whole plant.

Further, in the latter case, although inoculation of the recombinant transcription vector into tobacco was successful, it was found that the vector did not systemically move from the inoculated leaf.

Further, in both cases, replication ability was lowered to $10^{-2}$ to $10^{-3}$ compared to the natural virus.

The above described problems become practically fatal drawbacks when plants are transformed using the RNA vectors or when useful proteins are produced using the vectors.

Thus, it is necessary to satisfy the following points for using plant RNA viruses as a vector:

(1) Such a virus has a high replication ability in plant cells;

(2) When an exogenous DNA fragment is inserted into the virus nucleic acid, the virus can maintain biological activity;

(3) It is desirable that the virus is systemically infectious; and (4) The virus has a host range as wide as possible.

SUMMARY OF THE INVENTION

The object of the invention is to provide a vector which satisfies the conditions required as a vector and is capable of effectively conducting transformation and the production of useful proteins.

That is, the present invention relates to a vector comprising a satellite RNA of a plant virus, and the vector is constructed by inserting an exogenous RNA fragment into a satellite while its replication ability is maintained within the limits of the possibilities to change it to a chimeric RNA molecule.

More specifically, such a construction can be attained by connecting the exogenous RNA between the 5'-terminal sequence and the 3'-terminal sequence of the satellite in a way whereby the RNA is replicable in messenger sense.

The invention is described along with the change of satellite RNA (Y strain) of CMV having a very wide host range, as an example.

The restriction enzyme map of cDNA of the satellite RNA of CMV (Y strain) used herein is shown in FIG. 3 and the base sequence is shown in FIG. 4.

Satellite RNAs used in the invention are not limited to those derived from CMV, and those having the same effect in spite of the difference in a partial base sequence fall within the invention.

CMV satellite RNA replicates well in the presence of CMV, and competes with CMV genome RNA for the replication enzyme, thus reducing the multiplication of the genome RNA and may lead to reduction of the symptoms of CMV.

From the analysis of its base sequence are estimated several open reading frames (ORF), but there has been no demonstration that any product (protein) from these ORFs had actually been detected.

If CMV satellite RNA encodes no functional protein, it means that ORF destroyed by the insertion of an exogenous RNA fragment does not exist and is convenient for changing into vector.

A vector of the invention can be created by inserting an exogenous RNA fragment into CMV satellite RNA in a way whereby the replication ability of the CMV satellite RNA is spoiled as little as possible.

Specific steps therefor are shown below.

(1) Full-length of cDNA of CMV satellite RNA is prepared (FIG. 4)

(2) The cDNA is integrated into a DNA transcription vector (3) Infectious RNA is regenerated by in vitro transcription (4) The sequence of center part of the cDNA is excised with a restriction enzyme, and an exogenous DNA fragment is inserted (5) In vitro transcription is carried out using an RNA polymerase (6) The above transcript and CMV are simultaneously inoculated into a leaf of a plant For synthesizing the corresponding infectious transcript in vitro from the cDNA of CMV satellite RNA it is unnecessary to attach thereto the cap structure which a natural satellite has at the 5'-terminus.

However, attachment of non-viral sequence derived from the transcription vector to the 5'- or 3'-terminus of the transcript strikingly decreases the infectivity of the transcript.

It is possible to use pUT118 or pUT118GG as a transcription vector in order not to attach an extra sequence at the 5'-terminus as far as possible [Kuwata et al.: Showa 63 nendo Nippon Shokubutsu Byori Gakkai Taikai Koen Yoshi Shu (Lecture Gists in Japan Plant Pathology Society Annual Meeting 1988 (April, 1988)].

pUT118 attaches two bases to the 5'-terminus of the inserted satellite.

Further, even when long extra bases are attached, for example by using a commercially available transcription vector, an infectious satellite can be obtained by synthesizing the deoxyoligonucleotide complementary to its non-viral sequence part, annealing it to the transcript RNA and then using RNaseH [Masuta et al.: Nucl. Acids. Res. 15, p10048 (1987)].

Further, as for the 3'-terminus of the RNA, recognition sequence of SmaI is preserved by insertion of the cDNA into the SmaI site of the transcription vector since CMV satellite RNA is completed by $—CCC_{OH}$.

Therefore, no extra nucleotide is attached to the 3-terminus of the run-off transcript from the recombinant transcription vector linearized with SmaI.

It is also desirable, when other satellites are used, to make a device to attach non-viral bases to the 3'-terminus as less as possible, for example to provide a suitable restriction enzyme site immediately after the 3'-terminus of the cDNA.

Since a virus used as a vector in the invention is a satellite, simultaneous inoculation thereof with the helper virus is necessary.

It is desirable to use as a helper virus one of mild strain so as not to cause severe symptoms on plants.

The full-length cDNA of CMV satellite RNA can easily be synthesized by a conventional method using oligonucleotide primers complementary to the 3'-termini of the (+) chain and (−) chain.

After cloning of this cDNA, for example, to the SmaI site of a commercially available transcription vector pIBI 31 (trade name: produced by IBI CO.) as shown in FIG. 1, transcription is carried out in vitro with T3 RNA polymerase whereby the satellite RNA having 24 extra bases at the 5'-terminus is obtained.

In FIG. 1, T3 represents the promoter of T3 phage.

This non-viral sequence part is specifically excised with RNaseH which recognises DNA-RNA hybrids alone to obtain an infectious RNA molecule.

Next, the center part of the cDNA of a satellite RNA is cleaved or removed, as shown in FIG. 2, with a suitable restriction enzyme such as BamHI, StyI, NheI or AsuII, and into this part is inserted a desired exogenous DNA fragment to a direction wherein the transcript RNA has messenger sense of antisense.

There may be partial deletion, change or insertion in the base sequence of the central part since this sequence does not have any influence on the nature for a vector.

Construction of the above recombinant vector can readily be attained by a series of manipulations of cleavage with a restriction enzyme, blunting with Klenow fragment and ligation reaction.

Alternatively, after extraction of the desired plasmid from a transformed *Escherichia coli* (FERM BP-2543) by a method disclosed, for example in Maniatis, T., Fritsch, E. F., and Sambrook, J. (1982), Molecular Cloning, the desired base sequence is inserted inside a satellite RNA by gene manipulation.

The resulting recombinant plasmid is cleaved with a restriction enzyme SmaI and transcribed with RNA polymerase, and the resulting RNA is inoculated together with CMV into a tobacco blade, whereby a vector of the invention can also be obtained.

*Escherichia coli* strain transformed with the expression vector containing the cDNA of the satellite RNA (Y strain) had been deposited as FERM P-10756 on May 31, 1989 with the Fermentation Research Institute, Agency of Industrial Science and Technology, the Ministry of International Trade and Industry located in Ibaraki-ken, Japan, and was transferred to the International deposit in the Fermentation Research Institute on Aug. 2, 1989 and given as accession number FERM BP-2543.

It is possible to introduce an exogenous DNA fragment into plant cells and multiply it, using a vector of the invention.

A vector of the invention can move throughout the plant using a peculiarity of satellite RNAs, which other RNA viruses do not have, that a satellite is integrated in the viral particle of its helper virus.

Since host range in case of CMV is wide and 190 or more kinds of plants belonging to 45 families of herbs and arbores of dicotyledons and monocotyledons are infected with CMV, vectors of the invention can be utilized in a very wide range of plants.

Examples of the use of vectors of the invention are described below.

A vector of the invention can simultaneously be inoculated together with its helper virus into cells of a plant to integrate the exogenous gene therein, whereby transformation of the plant can be carried out.

For example, a virus-resistant plant can be created by introducing the antisense sequence of the plant virus in the plant to transform it.

Further, it is possible to simultaneously inoculate a vector of the invention with its helper virus into cells of a plant to integrate the exogenous gene therein and then produce a useful gene product based on the gene.

For example, it is possible to utilize a plant or culture cells of a plant as a place for production of useful protein such as a physiologically active peptide by integration of the gene of the peptide.

Although usual vectors have been integrated into a basic gene on the chromosome, vectors of the invention act on an extranuclear gene and thus have no bad influence on the plants.

Vectors of the invention can be replicated with a fairly good efficiency so long as the insertion site of an exogenous RNA fragment is contrived, and moreover, when satellite RNAs are modified, the vectors may be contained in particles of their helper viruses and move throughout the plant.

This means the distribution of an antisense RNA against a virus or the like to the whole plant body, and that production of a useful protein or peptide is carried out in the whole plant body based on the gene information thereof integrated in the vector.

As is seen from the above, it is possible according to the invention to satisfy conditions necessary as a vector and to effectively carry out transformation of plants, synthesis of proteins, etc.

BRIEF DESCRIPTION OF DRAWINGS

Figure 3:
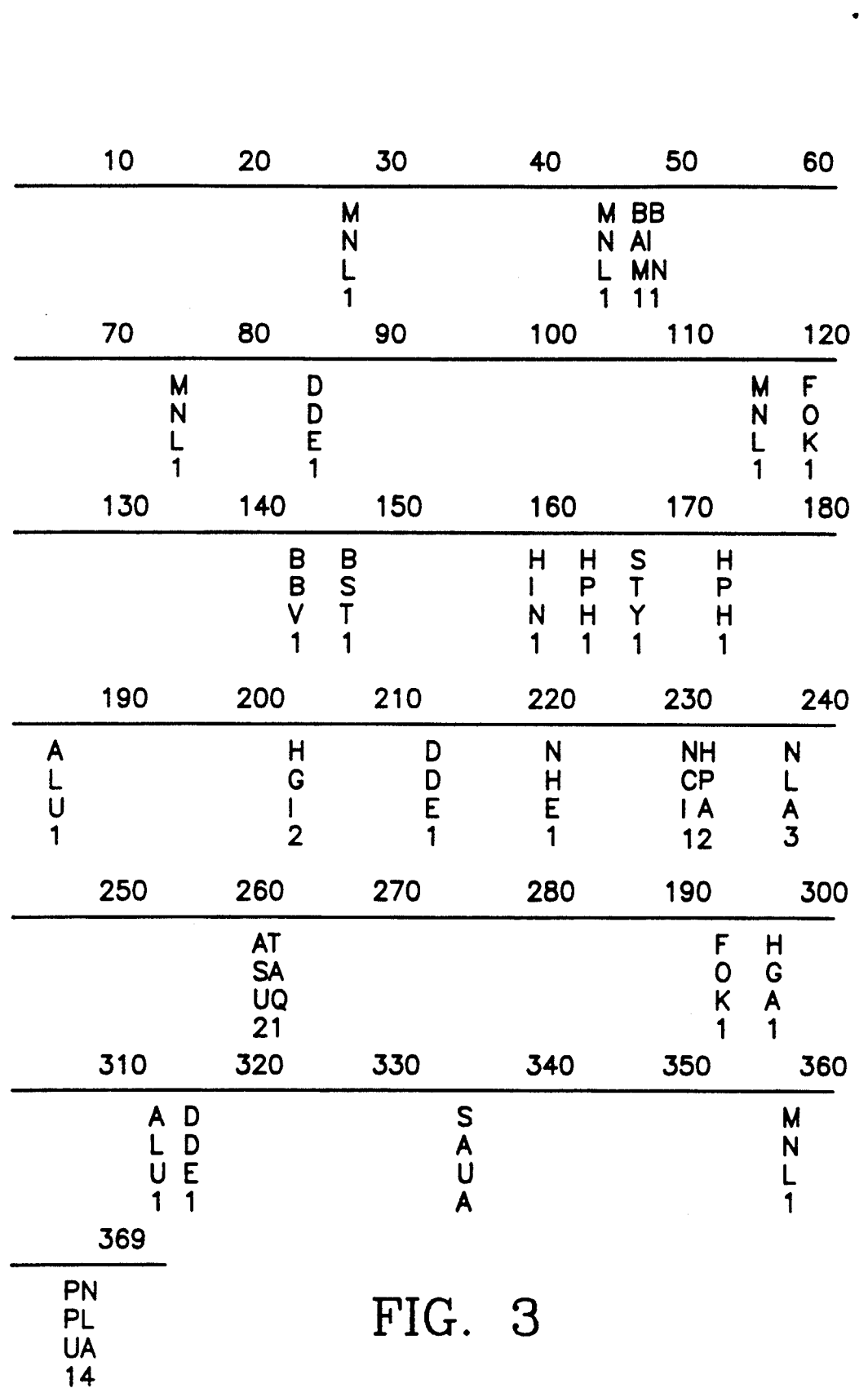

FIG. 3 shows the restriction enzyme map of cDNA of satellite RNA (Y strain) of CMV.

FIG. 4 shows the base sequence of satellite RNA (Y strain) of CMV.

DESCRIPTION OF THE PREFERRED EMBODIMENTS

Preparation of satellite RNA (Y strain)

(a) Separation of CMV satellite RNA

Total nucleic acids were extracted according to the phenol-SDS method from diseased leaves of a strain attacked with desease seemed to be infected with CMV in a tobacco field.

The extract was electrophoresed with 2 to 4% agarose gel and nucleic acids containing Y-satellite RNA were detected.

This judgement can easily be conducted using double-strand nucleic acids as a marker.

Y-satellite RNA is directly cut out from agarose gel and recovered from gel by electroelution, and the nucleic acid was precipitated with ethanol.

Alternatively, satellite RNA can be obtained by extracting viral nucleic acids from purified CMV with phenol, recovering fractions containing satellite RNA by sucrose-density gradient centrifugation and subjecting the fractions to ethanol preciptation.

Thus obtained nucleic acids were used for the following inoculation test and cloning.

(b) Cloning and base sequence determination

The cDNA of CMV satellite RNA was prepared according to a method wherein the method of Gubler and Hoffman is improved.

Specifically, a 17-mer deoxyoligonucleotide which anneals to the 3'-terminus of the satellite RNA is synthesized, and reverse transcriptase is made to act on the 17-mer as a primer to synthesize a complementary DNA.

After decomposition of the RNA chain of purified RNA-DNA hybrid with RNaseH, the resulting cDNA was double-stranded with DNA polymerase using the 17-mer synthetic deoxyoligonucleotide as a primer to obtain a full-length double-stranded cDNA.

Each of the above manipulations is known and was carried out according to the method disclosed in J. Biochem. 104, 841-846 (1988).

The cDNA of the Y-satellite RNA was cloned to the SmaI site of a commercially available plasmid vector pUC 119.

This recombinant plasmid (pUC 119-S) was denatured by the alkali method and its base sequence, shown in FIG. 4, was determined by the Sanger method.

Construction of pIBI 31-MC

The full length chain cDNA (FIG. 4) of CMV satellite RNA (Y strain) synthesized by a conventional method using the oligonucleotide primers complementary to the 3'-terminus of (+) chain and (−) chain was cloned into the SmaI site of pUC13 and a recombinant plasmid pC3 was selected. Both the 5'-terminus and 3'-terminus of the 390b XbaI/SacI fragment of this pC3 were blunted with Klenow fragment and T4DNA polymerase.

On the other hand, the polylinker site of a DNA transcription vector pIBI 31 was removed with EcoRI and HindIII, blunting was carried out with Klenow fragment, and linking was carried out using the above XbaI/SacI fragment and T4DNA ligase to construct pIBI 31-MC.

Production of an infectious transcript

The above pIBI 31-MC was linearized by cleavage with SmaI, and transcription was carried out using the resulting product as a template for T3 RNA polymerase. As a result, a product having a very low infectivity ($10^{-3}$ to $10^{-4}$ of natural satellite) was produced wherein 24 extra bases are linked to the 5'-terminus of the transcript.

Figure 1:
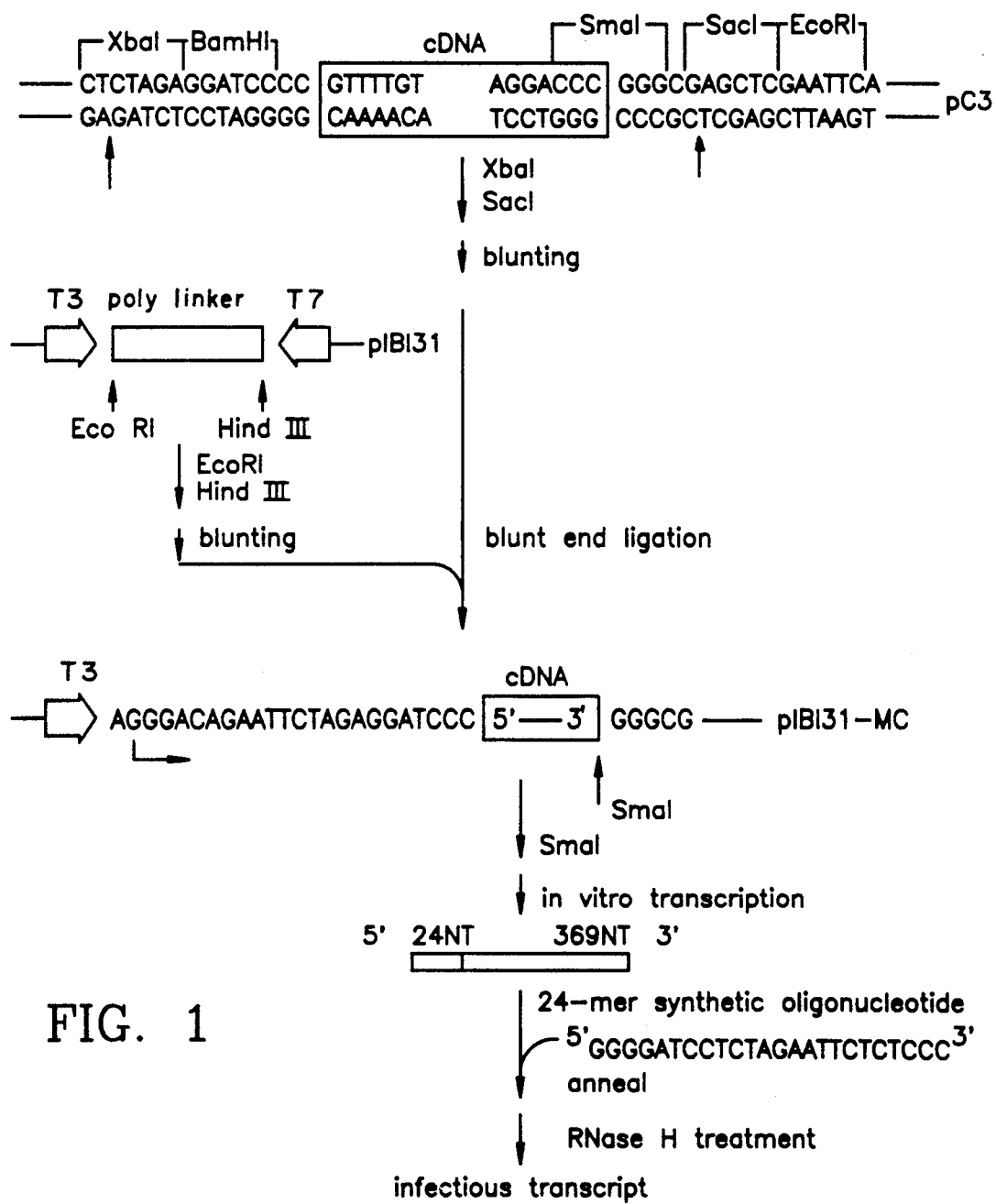
FIG. 1 shows a drawing giving an outline of construction of a recombinant transcription vector pIBI 31-MC for in vitro regeneration of an infectious satellite RNA, and excision of non-viral sequence part with RNaseH.

In order to excise the non-viral sequence at the 5'-terminus, the 24-mer deoxyoligonucleotide complementary thereto was synthesized and after annealing it to the transcript RNA, the resulting DNA-RNA hybrid portion was specifically digested with RNaseH (Reaction was carried out at room temperature for 40 minutes in a reaction solution containing 50 mM Tris-HCl, pH 7.5, 75 mM KCl, 3 mM $MgCl_2$, 100 mM DTT, RNA/oligonucleotide=1/10 (molar ratio) and 1U RNaseH) (FIG. 1).

The resulting product obtained by this RNaseH treatment exhibited an infectivity to the same extent as the natural satellite RNA.

Construction of pSC4

Figure 2:
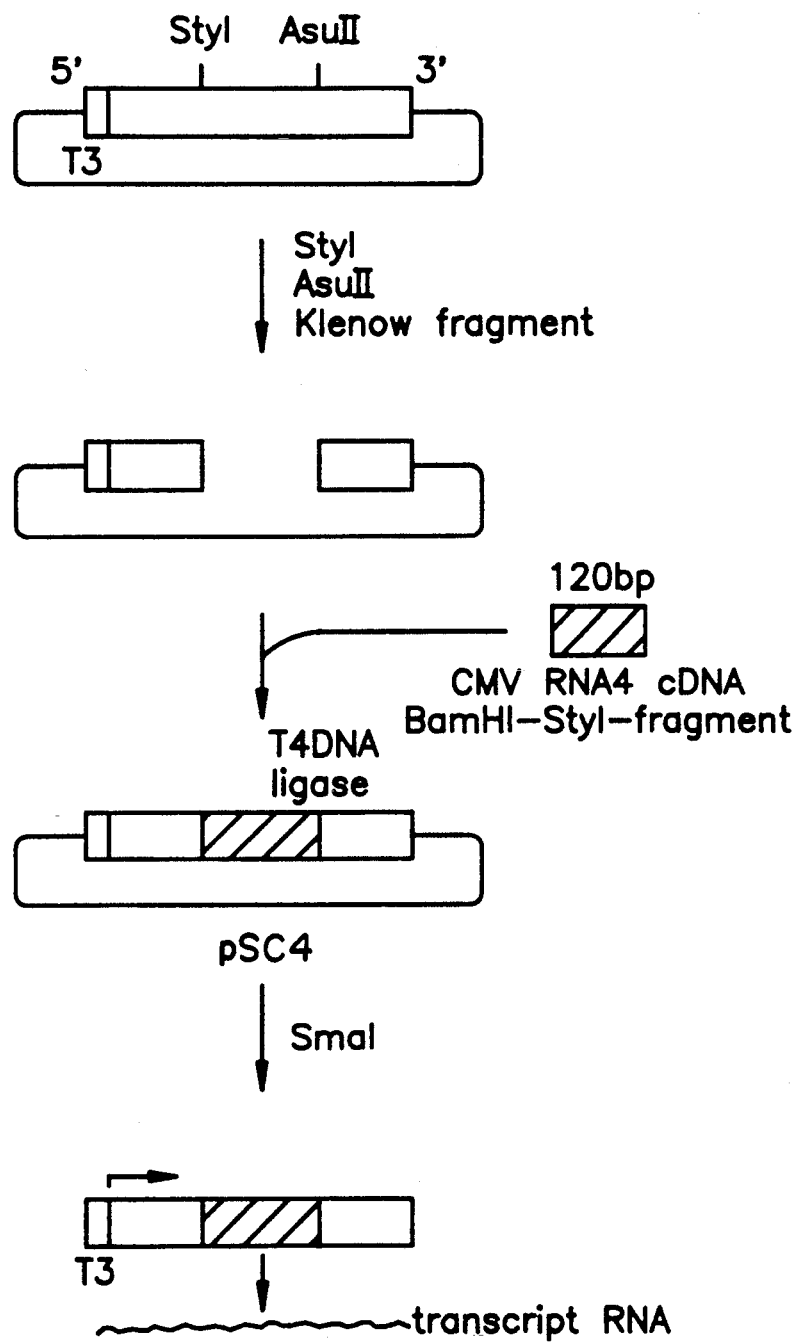
FIG. 2 shows a drawing giving an outline of construction of pSC4 as an example of transcription vectors.

The 90b StyI/AsuII fragment was excised from the above pIBI 31-MC, and the terminus of the resulting plasmid was blunted with Klenow fragment. To this part was linked in a cis-form the 120b DNA fragment of the 3'-terminal part of CMVRNA4 (Ann. Phytopath. Soc. Japan., Vol. 54, 408 (1988)) with T4 DNA ligase (FIG. 2).

The DNA-RNA hybrid site of the transcript, when this recombinant plasmid pSC4 was used as a template, was specifically excised with RNaseH according to the above method. The resulting transcript was then simultaneously inoculated with tobacco CMV of 40 days after seeding into a leaf of tobacco.

Nucleic acids were extracted from an upper leaf one week thereafter and immobilized onto a nitrocellulose membrane, and dot blot hybridization was carried out, whereby replication of this vector in a yield of ∼10 ngRNA/g viable leaf was confirmd.

Construction of pSY-T pSY-T was constructed in the same manner as in pSC4 by integrating the 120bp cDNA fragment of potato virus Y (T strain) (PVY-T) in the StyI/AsuII region of the above pIBI 31-MC in a direction wherein the fragment has (−) sense when transcribed.

The DNA-RNA hybrid portion of the transcript from this pSY-T was specifically digested with RNaseH according to the above-mentioned method. The resulting products and a mild CMV were then simultaneously inoculated in tobacco, and one week thereafter was detected the vector by dot blot hybridization in a yield of ∼1ngRNA/g viable leaf.

PVY-T was then inoculated into this tobacco and change of symptom had been observed for 3 weeks. As a result, the symptom of gangrene due to PVY-T was reduced in the tobacco wherein multiplication of the vector was confirmed.

Creation of the infectious satellite RNA from *Escherichia coli* and preparation of its cDNA Steps to obtain the cDNA of the infectious satellite RNA from the deposited *Escherichia coli* are described below.

A single colony of the transformed *Escherichia coli* (FERM BP-2543) was cultured overnight at 37° C. in 2 ml of the LB liquid medium.

One (1) ml of this culture broth was centrifuged for harvest.

The obtained microbial cells were suspended in 200 μl of a solution (pH 8.0) consisting of 50 mM glucose, 10 mM EDTA and 25 mM Tris-HCl.

0.5 mg of lysozyme (10 mg/ml) was added thereto, and after allowing to stand for 5 minutes, 400 μl of a solution containing 0.2N NaOH and 1% sodium dodecyl sulfate was added, followed by allowing to stand at 0° C. for 10 minutes.

Then, 300 μl of 3M potassium acetate, followed by allowing to stand at 0° C. for 15 minutes and succesively at 65° C. for 15 minutes.

The reaction solution was centrifuged, and after addition of 600 μl of isopropanol to the supernatant further centrifuged. The precipitate was suspended in 20 μl of water to obtain a plasmid containing the cDNA of the satellite RNA (Y strain) from *Escherichia coli*.

The resulting plasmid was cleaved with a restriction enzyme SmaI and then subjected to reaction at 37° C. for one hour in a mixed solution (pH 8.0) consisting of 40 mM Tris-HCl, 5 mM MgCl$_2$, 2 mM spermidine-HCl, 10 mM NaCl, 10 mM dithiothreitol, 1 mM ATP, 1 mM CTP, 1 mM GTP, 1 mM UTP, 20 unit RNasin (produced by Takara Shuzo Co., Ltd.) and 10 unit T7RNA polymerase (produced by Boehringer Co.).

This reaction solution was inoculated together with CMV into a leaf of tobacco, and 7 days thereafter, all the nucleic acids were extracted from diseased leaves according to the phenol-SDS method.

The resulting nucleic acids were fractionated in a 2% agarose gel, the band of satellite RNA was cut out, and the satellite RNA was recovered by electroelution and precipitated with ethanol to obtain an infectious satellite RNA.

We claim:

1. A method for transforming a plant which method comprises simultaneously inoculating said plant with a recombinant RNA vector and CMV helper virus to introduce an exogenous gene into cells of said plant, wherein said RNA vector comprises an exogenous gene integrated into CMV satellite RNA.

2. A method for producing a useful RNA which method comprises simultaneously inoculating a plant with a recombinant RNA vector and CMV helper virus to introduce an exogenous gene into cells of said plant, wherein said plant cells then produce RNA encoded by said vector, wherein said RNA vector comprises an exogenous gene integrated into CMV satellite RNA.

3. An infectious recombinant RNA vector comprising (a) RNA corresponding to an exogenous gene, said exogenous gene comprising a 120 bp CMV RNA4 cDNA BamHI/StyI fragment and (b) RNA corresponding to pIBI 31-MC lacking a 90 bp StyI/AsuII fragment of plasmid pIBI 31-MC.

4. An infectious recombinant RNA vector comprising (a) RNA corresponding to an exogenous gene, said exogenous gene comprising a 120 bp cDNA fragment of potato virus Y (T strain) and (b) RNA corresponding to pIBI 31-MC lacking a 90 bp StyI/AsuII fragment of plasmid pIBI 31-MC.

5. The method according to claim 1, wherein said RNA vector comprises (a) RNA corresponding to an exogenous gene, said exogenous gene comprising a 120 bp CMV RNA4 cDNA BamHI/StyI fragment and (b) RNA corresponding to pIBI 31-MC lacking a 90 bp StyI/AsuII fragment of plasmid pIBI 31-MC.

6. The method according to claim 1, wherein said RNA vector comprises (a) RNA corresponding to an exogenous gene, said exogenous gene comprising a 120 bp cDNA fragment of potato virus Y (T strain) and (b) RNA corresponding to pIBI 31-MC lacking a 90 bp StyI/AsuII fragment of plasmid pIBI 31-MC.

7. The method according to claim 2, wherein said RNA vector comprises (a) RNA corresponding to an exogenous gene, said exogenous gene comprising a 120 bp CMV RNA4 cDNA BamHI/StyI fragment and (b) RNA corresponding to pIBI 31-MC lacking a 90 bp StyI/AsuII fragment of plasmid pIBI 31-MC.

8. The method according to claim 2, wherein said RNA vector comprises (a) RNA corresponding to an exogenous gene, said exogenous gene comprising a 120 bp cDNA fragment of potato virus Y (T strain) and (b) RNA corresponding to pIBI 31-MC lacking a 90 bp StyI/AsuII fragment of plasmid pIBI 31-MC.

9. The method according to claim 1, wherein said plant is tabacco.

10. The method according to claim 2, wherein said plant is tobacco.

11. A plant into which has been introduced CMV helper virus and an infectious recombinant RNA vector selected from the group consisting of (i) RNA vector comprising (a) RNA corresponding to an exogenous gene, said exogenous gene comprising a 120 bp CMV RNA4 cDNA BamHI/StyI fragment and (b) RNA corresponding to pIBI 31-MC lacking a 90 bp StyI/AsuII fragment of plasmid pIBI 31-MC and (ii) RNA vector comprising (a) RNA corresponding to an exogenous gene, said exogenous gene comprising a 120 bp cDNA fragment of potato virus Y (T strain) and (b) RNA corresponding to pIBI 31-MC lacking a 90 bp StyI/AsuII fragment of plasmid pIBI 31-MC.

* * * * *